United States Patent [19]

Walker

[11] 4,272,545

[45] Jun. 9, 1981

[54] DERIVATIVES OF THIENYL- AND FURYL-SUBSTITUTED N-BUTYL AND N-PHENYL IMIDAZOLES

[75] Inventor: Keith A. M. Walker, Los Altos Hills, Calif.

[73] Assignee: Syntex (U.S.A.) Inc., Palo Alto, Calif.

[21] Appl. No.: 8,718

[22] Filed: Feb. 2, 1979

[51] Int. Cl.³ .................... A01N 43/50; C07D 403/00
[52] U.S. Cl. ........................ 424/273 R; 548/336; 548/341
[58] Field of Search ............................ 548/336, 341; 424/273 R

[56] References Cited

U.S. PATENT DOCUMENTS

| | | | |
|---|---|---|---|
| 3,658,813 | 4/1972 | Godefroi et al. | 548/341 |
| 3,717,655 | 2/1973 | Godefroi et al. | 548/336 |
| 4,017,631 | 4/1977 | Janssen et al. | 548/336 |
| 4,045,568 | 8/1977 | Walker | 424/273 R |
| 4,062,966 | 12/1977 | Gymer | 548/336 |
| 4,078,071 | 3/1978 | Walker | 424/273 R |
| 4,107,314 | 8/1978 | Cox et al. | 548/341 |
| 4,123,542 | 10/1978 | Walker | 542/413 |

*Primary Examiner*—Ethel G. Love

*Attorney, Agent, or Firm*—Annette M. Moore; Tom M. Moran; Alan M. Krubiner

[57] ABSTRACT

The compounds of the present invention are represented by the formula

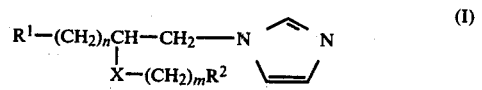

wherein $R^1$ and $R^2$ are the same or different and are optionally substituted furyl or thienyl the substituents independently selected from the group halo, $C_1$ to $C_6$ alkyl and $C_1$ to $C_6$ alkoxy or optionally substituted phenyl the substituents independently selected from the group halo, $C_1$ to $C_4$ alkyl, $C_1$ to $C_4$ alkoxy and trifluoromethyl; X is oxygen or sulfur; m is the integer 0; and n is the integer 2 or 3; and the antimicrobial acid addition salts thereof, with the proviso that when either $R^1$ or $R^2$ is said optionally substituted phenyl the other $R^1$ or $R^2$ is said optionally substituted furyl or thienyl.

The compounds are useful for combatting fungi, bacteria and protozoa. They also have spermatocidal and spermatostatic activity.

10 Claims, No Drawings

DERIVATIVES OF THIENYL- AND FURYL-SUBSTITUTED N-BUTYL AND N-PHENYL IMIDAZOLES

DETAILED DESCRIPTION OF THE INVENTION

The present invention relates to novel chemical compounds which are derivatives of substituted N-alkyl imidazoles. More particularly, the compounds of the present invention are represented by the formula

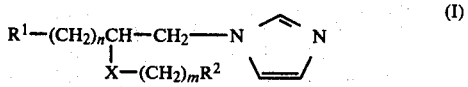

wherein $R^1$ and $R^2$ are the same or different and are optionally substituted furyl or thienyl the substituents independently selected from the group halo, $C_1$ to $C_6$ alkyl and $C_1$ to $C_6$ alkoxy or optionally substituted phenyl the substituents independently selected from the group halo, $C_1$ to $C_4$ alkyl, $C_1$ to $C_4$ alkoxy and trifluoromethyl; X is oxygen or sulfur; m is the integer 0; and n is the integer 2 or 3; and the antimicrobial acid addition salts thereof, with the proviso that when either $R^1$ or $R^2$ is said optionally substituted phenyl the other $R^1$ or $R^2$ is said optionally substituted furyl or thienyl.

In a second aspect, the present invention is concerned with a method of combatting fungi, bacteria and protozoa by administering a compound of the present invention or a composition containing such compound.

As used in the specification and the appended claims, unless specified to the contrary, the following terms have the meaning indicated. The term "$C_1$ to $C_6$ alkyl" refers to a straight or branched chain substituent consisting solely of carbon and hydrogen, containing no unsaturation and having from one to six carbon atoms. Examples of such alkyl groups are methyl, ethyl, n-propyl, i-propyl, n-butyl, t-butyl, pentyl and n-hexyl. The term "$C_1$ to $C_6$ alkoxy" refers to 1 to 6 carbon-containing alkyl groups, linked thru an ether linkage and having the free valence from the ether oxygen. Examples of such groups include methoxy, ethoxy, n-propoxy, i-propoxy, n-butoxy, t-butoxy, n-hexyloxy and the like. The term "halo" refers to fluoro, chloro and bromo. "Antimicrobial acid addition salts" of the subject bases refers to those salts which retain the antimicrobial properties of the free bases and which are neither biologically or otherwise undesirable, formed with, for example, inorganic acids such as hydrochloric acid, hydrobromic acid, sulfuric acid, nitric acid or phosphoric acid; or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like. The term "optionally substituted furyl or thienyl" is intended to refer to unsubstituted or substituted furyl or thienyl groups. When such are substituted, these groups may have one, two or three substituents independently selected from the group halo, $C_1$ to $C_6$ alkyl and $C_1$ to $C_6$ alkoxy. Similarly, the term "optionally substituted phenyl" is intended to mean an unsubstituted or substituted phenyl group. When such is substituted the phenyl group may have from one to five substituents independently selected from the group halo, $C_1$ to $C_4$ alkyl, $C_1$ to $C_4$ alkoxy and trifluoromethyl. When more than 3 substituent are present these are the same and are chloro or methyl. It is also understood, for purposes of this invention, that the phenyl rings of $R^1$ and $R^2$ cannot be substituted with adjacent branched alkyl and/or trifluoromethyl groups. It should be particularly pointed out that, in the compounds of the present invention, when either of $R^1$ or $R^2$ is the optionally substituted phenyl group as defined above, the other $R^1$ or $R^2$ must be either the optionally substituted furyl or thienyl group.

All compounds of formula (I) possess at least one chiral center, i.e., the carbon atom to which are attached the moieties X, $R^1(CH_2)_n$, $CH_2$ and H. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form but to encompass the individual optical isomers of the subject compounds.

If desired, racemic intermediates or final products described herein may be resolved into their optical antipodes by conventional resolution means known per se, for example, by the separation (e.g, fractional crystallization) of the diastereomeric salts formed by reaction of the racemic compounds of formula (I) with an optically active acid, or by the separation of the diastereomeric salts or esters formed by reaction of racemic compounds of formula (II), infra, with an optically active acid. Exemplary of such optically active acids are the optically active forms of camphor-10-sulfonic acid, $\alpha$-bromo-camphor-$\pi$-sulfonic acid, camphoric acid, methoxyacetic acid, tartaric acid, malic acid, diacetyltartaric acid, pyrrolidone-5-carboxylic acid, dibenzoyltartaric acid and the like. The separated pure diastereomeric salts or esters may then be cleaved by standard means to afford the respective optical isomers of the compounds of formulas (I) or (II).

The subject compounds of formula (I) exhibit antifungal, antibacterial and antiprotozoal activity. For example, compounds of the present invention exhibit antifungal activity against human and animal pathogens, including the following:

*Microsporum audouini;*
*Microsporum gypseum;*
*Microsporum canis;*
*Epidermophyton floccosum;*
*Trichophyton mentagrophytes;*
*Trichophyton rubrum;*
*Trichophyton tonsurans;*
*Trichophyton concentricum;*
*Candida albicans;* and
*Cryptococcus neoformans.*

The compounds of the present invention also exhibit antifungal activity against the following fungi primarily of agricultural significance:

*Aspergillus flavus;*
*Aspergillus niger;*
*Cladosporium herbarum;*
*Penicillium oxalicum;*
*Fusarium graminearum;*
*Penicillium spinulosum;*
*Penicillium notatum;* and

*Pithomyces chartarum.*

In addition, the compounds of the present invention exhibit antibacterial activity against human and animal pathogens, including the following:
*Staphylococcus aureus;*
*Streptococcus faecalis;*
*Corynebacterium acnes;*
*Erysipelothrix insidiosa;*
*Escherichia coli;*
*Proteus vulgaris;*
*Salmonella choleraesuis;*
*Pasteurella multocida;* and
*Pseudomonas aeruginosa.*

Moreover, the compounds of the present invention exhibit anti-protozoal activity against protozoa such as *Trichomonas vaginalis* and *Trichomonas foetus.*

In general, the subject compounds of the instant invention exhibit a low level of toxicity. Moreover, these compounds demonstrate good solubility in the stratum corneum. Since dermatophyte (i.e., parasitic fungal) infections are usually localized in the dead tissue of the stratum corneum, solubility of antifungal agents in this tissue significantly enhances their effectiveness.

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural and industrial use, which compositions comprise the subject compounds of formula (I) in combination with a suitable carrier. A still further aspect of the present invention relates to methods of inhibiting the growth of fungi, bacteria and protozoa by applying to a host object containing, or subject to attack by, fungi, bacteria or protozoa, an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, polyalkylene glycols, vaseline and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials. In pharmaceutical applications, the subject compounds and compositions may be administered to humans and animals by conventional methods, e.g., topically, orally, parenterally and the like. Parenteral administration includes intramuscular as well as subcutaneous and intravenous administration. Intravenous injection of imidazole-type antifungals has been demonstrated to be effective in the treatment of systemic mycoses (see for example, Drugs, 9, pp. 419–420, 1975, which describes the intravenous administration of miconazole, i.e. 1-[2,4-dichloro-$\beta$-(2',4'-dichlorobenzyloxy)phenethyl]imidazole nitrate, to patients with systemic candidiasis). Topical application is the preferred method of administration for pharmaceutical applications. For such treatment, an area having an existing fungal, bacterial or protozoal growth, or to be protected against attack by fungi, bacteria or protozoa, may be treated with the subject compounds or compositions by, for example, dusting, sprinkling, spraying, rinsing, brushing, dipping, smearing, coating, impregnating and the like. Topical pharmaceutical compositions containing the compounds of the present invention exhibit antifungal, antibacterial and antiprotozoal activity over a wide range of concentration, for example, from about 0.1 to 10.0% by weight of the composition. In any event, the composition to be administered will contain a quantity of the subject compound in an amount effective for relief or prevention of the specific condition being treated.

The pharmaceutical compositions hereof typically comprise one or more subject compounds of formula (I) and a pharmaceutically acceptable, non-toxic carrier and are preferably formulated in unit dosage form to facilitate administration (unit dosage being the amount of active ingredient administered on one occasion).

In general, for systemic (e.g., oral or parenteral) administration it is expedient to administer the active ingredient in amounts between about 1 and 100 mg./kg. body weight per day, preferably between about 5 and 50 mg./kg. body weight per day, preferably distributed over several applications (e.g., in 3 individual doses) in order to achieve most effective results. For localized (e.g. topical) administration, however proportionately less of the active ingredient is required.

The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner.

In agricultural applications, the subject compounds may be applied directly to plants (e.g., seeds or foliage) or to soil. For example, the compounds of the present invention may be applied to seeds alone or in admixture with a powdered solid carrier. Typical powdered carriers are the various mineral silicates, e.g., mica, talc, pyrophyllite and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agents, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

The compounds of formula (I) may be considered to consist of two subclasses, those of formulas (Ia) and (Ib) shown below

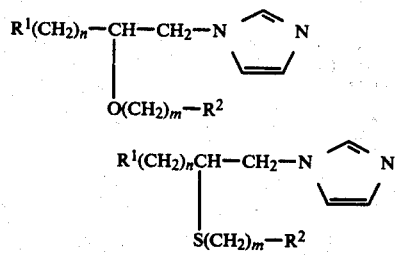

wherein $R^1$, $R^2$, m and n are as defined above.

Both groups of compounds may be prepared from common intermediates having a free hydroxyl group which is then converted to the ether or thioether, as the case may be, and which may be prepared by a variety of methods.

In either subgenus (Ia) or (Ib) it is preferred that only one $R^1$ or $R^2$ is the optionally substituted furyl or thienyl group, the other $R^1$ or $R^2$ being the optionally substituted phenyl group.

In the above preferred compounds of formula (Ia) or (Ib) when $R^1$ is a furyl or thienyl, the ring is preferably unsubstituted, or substituted with $C_1$ to $C_4$ alkyl, most preferably 5-methyl, $C_1$ to $C_4$ alkoxy, most preferably 5-methoxy or chloro or bromo, most preferably 5-chloro. Particularly preferred are those compounds wherein $R^1$ is selected from the group 5-chloro-2-thienyl, 5-methyl-2-thienyl, 2-furyl, 2-thienyl and 3-thienyl. In such preferred and most preferred compounds, $R^2$ is preferably phenyl substituted with one to five substituents selected from chloro, bromo, $C_1$ to $C_4$ alkyl and trifluoromethyl. When more than three substituents are present, these are the same and are methyl or chloro. When m is the integer zero, most preferably the substituents are selected from 2-chloro, 2,4-dichloro, 2,5-dichloro, 2,6-dichloro, 2,4,6-trichloro, 2,4,5-trichloro, 2-methyl, 2,4-dimethyl, 2,5-dimethyl, 2,6-dimethyl, 2,4,6-trimethyl, 2-methoxy, 2-methoxy-5-chloro, 2-chloro-5-methoxy, 2-chloro-6-methyl and 2-chloro-4,5-dimethyl. When m is the integer 1, preferred substituents on $R^2$ are 4-chloro, 4-methyl, 4-methoxy, 2,4-dichloro and 2,6-dichloro. In such $R^1/R^2$ preferred compounds, m is most preferably the integer 0, n is most preferably the integer 2, and X is most preferably sulfur when m is 0.

Particularly preferred are the following:
1-[4-(5-chloro-2-thienyl)-2-(2,6-dichlorophenylthio)-n-butyl]imidazole;
1-[4-(5-chloro-2-thienyl)-2-(2,5-dichlorophenylthio)-n-butyl]imidazole;
1-[4-(5-chloro-2-thienyl)-2-(2-chlorophenylthio)-n-butyl]imidazole; and
1-[4-(5-chloro-2-thienyl)-2-(2-chloro-6-methylphenylthio)-n-butyl]imidazole.

In the above compounds of formula (Ia) or (Ib) when $R^2$ is furyl or thienyl, such is preferably unsubstituted or substituted with $C_1$ to $C_4$ alkyl, most preferably methyl, methoxy, chloro or bromo, most preferably chloro. In such preferred and most preferred compounds, $R^1$ is preferably phenyl, mono-substituted with a substituent selected from fluoro, chloro, bromo, $C_1$ to $C_4$ alkyl, $C_1$ to $C_4$ alkoxy and trifluoromethyl. Most preferably the substituent is selected from 4-fluoro, 4-chloro, 4-bromo, 4-methyl, 4-ethyl, 4-i-propyl, 4-t-butyl, 4-methoxy, 4-ethoxy, 4-i-propoxy, 4-t-butoxy and 4-trifluoromethyl, with 4-methyl, 4-chloro or 4-methoxy being particularly preferred. In such preferred and most preferred compounds when m is the integer 1, particularly preferred are those compounds wherein $R^2$ is 2-thienyl, 3-thienyl, 5-chloro-2-thienyl, 2-chloro-3-thienyl, 2,5-dichloro-3-thienyl, 5-methyl-2-thienyl and 2-furyl. When m is the integer 0, particularly preferred are those compounds wherein X is sulfur and $R^2$ is 2-thienyl, 3-thienyl, 3-chloro-2-thienyl, 5-chloro-2-thienyl, 3-bromo-2-thienyl, 5-methyl-2-thienyl, 5-methoxy-2-thienyl, 3-methoxy-2-thienyl and 2-furyl. In such $R^1/R^2$ compounds, m is preferably the integer 0 and n is preferably the integer 2.

Particularly preferred are the following:
1-[4-(4-chlorophenyl)-2-(5-chloro-2-thienylthio)-n-butyl]imidazole;
1-[4-(4-chlorophenyl)-2-(2-thienylthio)-n-butyl]imidazole;
1-[4-(4-methylphenyl)-2-(5-chloro-2-thienylthio)-n-butyl]imidazole; and
1-[4-(4-chlorophenyl)-2-(3-chloro-2-thienylthio)-n-butyl]imidazole.

As disclosed above, compounds of formula (I) may be prepared by forming an ether or thioether from a suitable alcohol of formula (II)

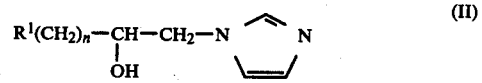

wherein $R^1$ and n are as defined above. Compounds of formula (II) may be prepared by a variety of reaction sequences, depending on the availability of starting materials and the nature of $R^1$.

For example, certain compounds of formula (II) may be prepared by reaction scheme A shown below.

Reaction Scheme A

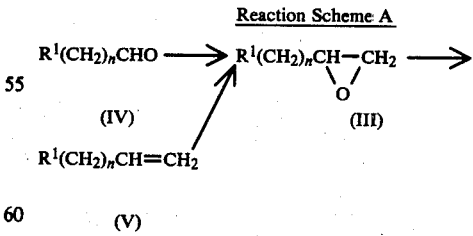

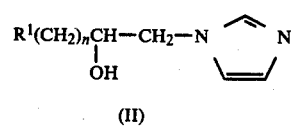

In this reaction scheme, the imidazole alcohol of formula (II) is formed by opening of the terminal epoxide of formula (III) with imidazole. This reaction is generally carried out using at least one mole and preferably an excess of imidazole relative to the epoxide. The reaction may either be carried out in the absence of solvent or, preferably, in an inert organic solvent, for example, a solvent such as dimethylformamide, tetrahydrofuran, hexamethylphosphoramide, acetonitrile and the like. The temperature normally employed for such epoxide ring-opening is in the range of from about $-20°$ to about 100° C. most preferably from about 20° to about 80° C. The epoxide ring-opening is preferably carried out using a salt of imidazole, e.g. an alkali metal salt, most preferably the sodium salt, in an inert organic solvent, such as tetrahydrofuran or dimethylformamide, at a temperture of from about $-20°$ to 100°, most preferably from 0° to 85°. The salt may be used stoichiometrically or most preferably catalytically in the presence of imidazole as a proton source.

Epoxides of formula (III), insofar as they may not be known or readily available, may be prepared by a variety of well known methods, for example epoxidation of a terminal olefin, e.g., reaction of (V) with a peracid, or by reaction of an aldehyde having one fewer carbon atom (e.g., (IV)) with the ylide prepared from trimethylsulfonium iodide or trimethylsulfoxonium iodide. See, for example, *J. Am. Chem. Soc.*, 84, p. 867 (1962); ibid, 87, p. 1353 (1965).

Another reaction scheme for preparing certain compounds of formula (II) is shown in reaction scheme B presented below.

Reaction Scheme B

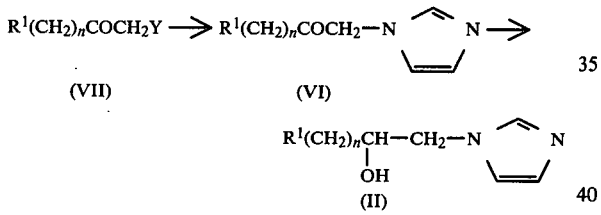

wherein Y is chloro or bromo and n and $R^1$ are as defined above.

In this reaction scheme, the hydroxy compound of formula (II) is prepared by reduction of the corresponding ketone (VI), which in turn is prepared by reaction of an α-halo ketone (VII) with imidazole.

α-Halo ketones insofar as they may not be generally available, may be readily prepared, for example from an acid halide of the formula $R^1(CH_2)_nCOCl$, where $R^1$ and n are defined above by first converting it to the diazoketone, $R^1(CH_2)_nCOCHN_2$ with diazomethane and subsequent treatment with a hydrohalic acid such as hydrogen chloride or hydrogen bromide. This α-halo ketone is contacted with imidazole to afford the keto imidazole of formula (VI). The reaction is carried out utilizing at least a molar amount and, preferably, an excess of imidazole relative to the halo ketone. The reaction may be carried out in the absence of solvent or, preferably, in an inert organic solvent such as for example dimethylformamide, hexamethylphosphoramide, acetonitrile and the like. The reaction is suitably conducted at a temperature initially between about $-10°$ and 100° C. most preferably between about 0° and 25° C.

The keto imidazole of formula (VI) is reduced to the hydroxy imidazole of formula (II) utilizing a conventional metal hydride reducing agent such as, for example, sodium borohydride. The reaction is suitably carried out in an alcoholic solvent such as, for example, methanol or ethanol at a reduced temperature, for example between about $-10°$ and 25° C., most preferably about 0° C.

Certain compounds of formula (II) may be prepared according to a further reaction sequence. This is illustrated below in reaction scheme C Reaction Scheme C

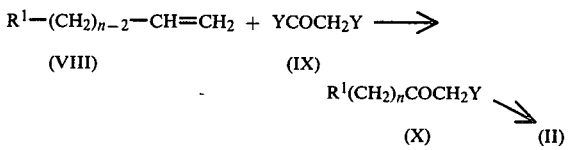

wherein Y is chloro or bromo and $R^1$ and n are defined above.

In this scheme the α-halo ketone of formula (X), described above, is prepared by treating a terminal olefin of formula (VIII) with an α-halo acetyl halide of formula (IX). This reaction is carried out under the conditions described in G. Olah, "Friedel Crafts and Related Reactions"; Vol. 3, Part 2, Interscience Publishers, New York (1964).

A preferred method for preparing compounds of formula (II) is illustrated in reaction scheme D, shown below Reaction Scheme D

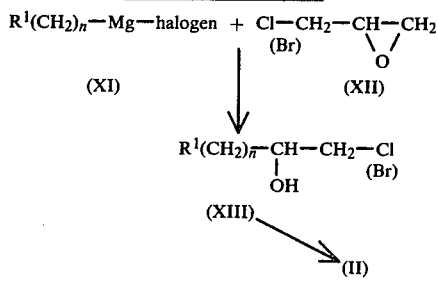

where $R^1$ is optionally substituted phenyl.

In this scheme the appropriately substituted benzyl or phenethyl Grignard reagent (XI) (preferably the benzyl or phenethyl magnesium chloride) is reacted with epichlorohydrin (or epibromohydrin) (XII) to afford the halohydrin (XIII). This reaction is carried out in typical solvents for perfoming Grignard reactions, namely ether-containing solvents, preferably diethyl ether and at temperatures between about 20° and 50° C.

The halohydrin (XIII) is then converted to the imidazole alcohol (II) by treatment with an alkali metal (preferably sodium) salt of imidazole in a polar aprotic solvent such as dimethylformamide at a temperature between about 50° and 100° C.

Alternatively, treatment of the halohydrin with base will afford the epoxide (III) described in Reaction Scheme A.

When $R^1$ is a heteroaromatic ring, the method shown above in Reaction Scheme D is modified as shown below in Reaction Scheme E.

Reaction Scheme E

-continued

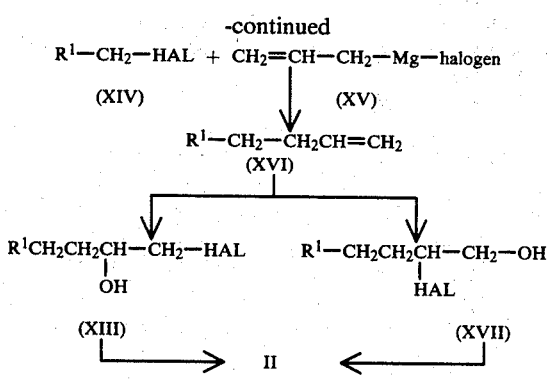

where $R^1$ is the optionally substituted furyl, thienyl or phenyl as previously defined and HAL is chloro or bromo.

In this scheme, the appropriately substituted halomethyl compound (XIV) is reacted with an allylmagnesium halide (XV) to give the butene (XVI), which is converted to the corresponding halohydrin (XIII) and/or (XVII). The halohydrin is then converted to the imidazole alcohol (II) as described above under Reaction Scheme D. The preparation of (XVI) is carried out in typical solvents for performing Grignard reactions, namely ether-containing solvents, at temperatures between about $-20°$ and $50°$ C.

The formation of the halohydrin(s) (XIII) and/or (XVII) may be carried out by a number of methods known to those skilled in the art, preferably using an N-halo amide, e.g., N-bromosuccinimide, N-bromoacetamide, etc. in an organic solvent such as wet dimethylsulfoxide or a neutral solvent such as dioxane in the presence of an acid catalyst.

The compounds of formula (II) are converted to the final products of formula (I) by a variety of methods depending on the nature of X, m and $R^2$. In one embodiment, the compounds of formula (II) are converted to the final products of formula (I) wherein X is oxygen, m is the integer 1 and $R^2$ is as previously defined by O-alkylation with the appropriate $R^2CH_2Y$ wherein Y is a leaving group such as halide (chloride, bromide or iodide) or sulfonate ester (e.g., p-toluenesulfonate or methanesulfonate). The alkylation is carried out by converting the hydroxy group of the compounds of formula (II) to the alkali metal salt by treatment with a strong base, for example, an alkali metal hydride such as sodium hydride, an alkali metal amide such as sodium amide or potassium amide and the like. This is preferably done in an inert organic solvent such as, for example, dimethylformamide, hexamethylphosphoramide, tetrahydrofuran and the like. The alkali metal salt is then contacted with $R^2CH_2Y$, preferably in the same solvent system, at a temperature between about $0°$ and $80°$, most preferably between about $0°$ and $60°$ C.

Compounds of formula (I) wherein m is 0 and $R^2$ is optionally substituted phenyl (i.e., phenolic ethers or thioethers) or wherein X is S, m is zero and $R^2$ is optionally substituted furyl or thienyl may be prepared from the compounds of formula (II) by a two-step reaction sequence involving conversion of the hydroxy group to a suitable leaving group such as a halide, e.g., a chloride or bromide, or a sulfonate ester, e.g., methanesulfonate or p-toluenesulfonate, which is then treated with the corresponding phenol $R^2$OH, thiophenol $R^2SH$ or heteroaromatic thiol (thienyl or furyl thiol), optionally in the presence of base, e.g., potassium carbonate or with a metal salt, preferably an alkali metal salt such as the lithium, sodium or potassium salt, of the phenol, thiophenol or heteroaromatic thiol.

The conversion from the alcohol to the halide or sulfonate ester is carried out by means well known in the art. For example, the alcohol may be halogenated using a halogenating agent such as thionyl chloride or thionyl bromide, without solvent, or in an inert organic solvent such as dichloromethane or chloroform, at a temperature between about $0°$ and $80°$ C., preferably between about $20°$ and $80°$ C. The halogenation reaction may be carried out in the presence of a molar equivalent of an organic or inorganic base (e.g., pyridine) if desired. Alternative halogenation procedures include, for example, the use of triphenylphosphine with either carbon tetrachloride, carbon tetrabromide or N-chloro (or N-bromo) succinimide. When utilizing thionyl chloride or thionyl bromide in the absence of a base, the hydrochloride or hydrobromide salt of the corresponding halo compound is produced. This salt may be neutralized (e.g., with potassium carbonate) prior to its use in the alkylation step, or the salt may be used directly if excess phenol, thiophenol or heteroaromatic thiol is utilized.

Sulfonate esters may be prepared by the standard procedure of treating the alcohol with an excess of, for example, methanesulfonyl chloride or p-toluenesulfonyl chloride, in the presence of a base, for example pyridine or triethylamine. This reaction is carried out at a temperature from about $-20°$ to $50°$ C., preferably between about $0°$ and $20°$ C.

The halide or sulfonate ester prepared as described above, is treated with the corresponding phenol, thiophenol or heteroaromatic thiol, optionally in the presence of a base, or with a metal salt (preferably of an alkali metal such as lithium, sodium or potassium) of the phenol, thiophenol or heteroaromatic thiol in the presence of an inert organic solvent such as acetone, methanol and the like, at a temperature of about $20°$ to about $80°$ C.

Salts of heteroaromatic thiols, in so far as they may not be known or readily available are prepared by in situ treatment of an appropriately ring-metallated (e.g., lithiated) heteroaromatic compound with sulfur prior to reaction with the halide or sulfonate ester.

Compounds of formula (I) wherein X is S, m is the integer 1 and $R^2$ is as defined above (i.e., optionally substituted furyl, thienyl or phenyl) may be prepared by reacting the above mentioned halide or sulfonate ester with the metal salt, preferably an alkali metal salt such as the sodium or potassium salt, of the thiol $R^2CH_2SH$. This reaction is carried out in an inert organic solvent such as, for example, tetrahydrofuran, diethylether, methanol and the like. The salt is formed with a strong base such as for example, sodium hydride, sodium amide, sodium methoxide and like, at a temperature between about $20°$ and $80°$ C.

In a preferred reaction, compounds of formula (I) wherein X is oxygen, m is the integer zero and $R^2$ is optionally substituted phenyl may be directly prepared from compounds of formula (II) in one step by reaction with the corresponding phenol in the presence of a triarylphosphine (preferably triphenylphosphine) and a dialkyl azodicarboxylate (preferably dimethyl or diethyl azodicarboxylate). This reaction is preferably carried out in an inert solvent such as an ether (preferably tetrahydrofuran or diethyl ether), a hydrocarbon (preferably benzene or toluene) or dimethylformamide at a temperature between about 0° and 40° C.

Compounds of formula (I) wherein X is S may also be prepared as depicted in Reaction Scheme F below

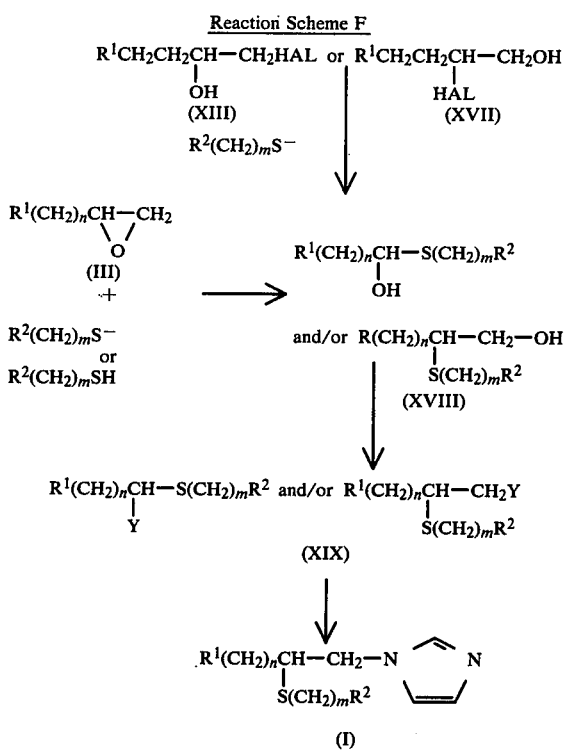

wherein Y is a leaving group, HAL is chloro or bromo and $R^1$, $R^2$, m and n are as previously defined.

In this scheme, the epoxide of formula (III) or the halohydrins (XIII) or (XVII) are treated with a thiol, thiophenol or metal salt thereof, to afford the compound of formula (XVIII). This reaction is carried out utilizing, preferably, an alkali metal salt of the thiol or thiophenol, most preferably the sodium salt, in an inert organic solvent such as, for example, tetrahydrofuran or acetone at a temperature of between about 0° and 67° C., or using the free thiol or thiophenol and the epoxide (III) in the presence of an acid catalyst, e.g., perchloric acid or boron trifluoride optionally in an inert organic solvent such as dichloromethane or nitromethane.

In the next step, the hydroxy group of the compounds of formula (XVIII) is converted to a leaving group such as a halo, e.g., chloro or bromo, or sulfonate ester, e.g., p-toluenesulfonate or methanesulfonate, by treatment with a halogenating agent such as thionyl chloride, in the absence of solvent or preferably in an inert organic solvent such as dichloromethane, or with, for example, p-toluenesulfonyl chloride, in a solvent such as tetrahydrofuran, dichloromethane and the like. The product of formula (XIX) may exist in either or both forms depicted and may be interconvertible through or isolable as an episulfonium salt.

In the final step, the compound of formula (XIX) is converted to the product of formula (I) by treatment with imidazole. This reaction is carried out in an inert organic solvent such as, for example, acetonitrile, dimethylformamide and the like, at a temperature of about 0° to about 80° C.

Certain compounds of formula (I) where X is S may also be prepared from compounds of formula (II) by reaction with a tri(loweralkyl)phosphine such as tri(n-butyl)phosphine and the corresponding sulfenimide as described in Tetrahedron Letters, No. 51, pp. 4475-4478 (1977).

The subject compounds of the instant invention can be isolated as free bases. In those cases where the compounds in their free-base form are oils, it is more convenient to isolate and characterize the compounds as acid addition salts. These salts are prepared in the usual manner, i.e., by reaction of the free-base with a suitable inorganic or organic acid, as described above. Salts formed with dibasic acids (e.g., oxalic acid) may generally contain one or two molecules of base per molecule of acid. All oxalates described herein contain one molecule of oxalic acid per molecule of imidazole base. If desired, the salts can be readily converted to the free base form by treatment with alkali, such as potassium carbonate, sodium carbonate, sodium hydroxide or potassium hydroxide.

Related compounds of the compounds of this invention of formula (I) are disclosed and claimed in U.S. application Ser. No. 758,094, filed Jan. 10, 1977, now U.S. Pat. No. 4,078,071. The preparative procedures described therein, are, in many cases, identical to the preparative procedures of this application. The relevant parts of this patent are therefore incorporated herein by reference.

A further understanding of the invention can be had from the following non-limiting Preparations and Examples. As used hereinabove and below unless expressly stated to the contrary, all temperatures and temperature ranges refer to the Centigrade system and the terms ambient or room temperature refer to about 20° C. The term percent or (%) refers to weight percent and the term mole and moles refers to gram moles. As noted earlier, compounds having assymetric centers and optical activity are isolated in their racemic form (±) unless otherwise indicated.

PREPARATION 1

1. A solution of allyl magnesium bromide (from 14.6 g of magnesium and 24.2 g (0.2 M) of allyl bromide) in 100 ml ether is added dropwise with stirring to 29.9 g of 5-chloro-2-chloromethylthiophene in 10 ml ether over half an hour and the resulting mixture heated under reflux overnight. The mixture is then poured into 300 ml ice cold dilute sulfuric acid, the ether layer separated and the aqueous phase extracted with 200 ml of ether. The combined ethereal solutions are washed with aqueous potassium carbonate, dried over $MgSO_4$ and evaporated to give crude 4-(5-chloro-2-thienyl)-1-butene as a yellow oil (34 g).

2. The crude olefin of step 1. in 100 ml dimethyl sulfoxide containing 7.2 g water is cooled to approximately 0° and treated with 71.2 g of solid N-bromosuccinimide in small portions over half an hour with efficient stirring. The resulting mixture is stirred overnight at room temperature, poured into 650 ml of water and extracted with ether (600 ml). The combined ethereal extracts are washed, dried over $MgSO_4$ and evaporated to give 38 g of a dark amber oil containing 1-bromo-4-(5-chloro-2-thienyl)-2-butanol and 2-bromo-4-(5-chloro-2-thienyl)-1-butanol.

3. Without purification the product mixture of step 2. in 20 ml dimethylformamide is added dropwise to a solution of sodium imidazole (from 3.16 g of 50% dispersion of sodium hydride in mineral oil and 4.8 g of imidazole) in 20 ml dimethylformamide with stirring at room temperature. The mixture is stirred overnight at 80°, poured into one liter of water and the mixture extracted with ether. After washing and drying over MgSO$_4$, the ether is removed and the residue chromatographed on silica gel eluting with 30% acetone in dichloromethane, followed by acetone to give the pure product. Recrystallization from toluene/hexane affords 1-[4-(5-chloro-2-thienyl)-2-hydroxy-n-butyl]imidazole, mp 82°–84.5°.

In a similar manner are prepared the following:

1-[4-(2-thienyl)-2-hydroxy-n-butyl]imidazole;
1-[4-(3-thienyl)-2-hydroxy-n-butyl]imidazole;
1-[4-(5-methyl-2-thienyl)-2-hydroxy-n-butyl]imidazole;
1-[4-(5-methyl-2-furyl)-2-hydroxy-n-butyl]imidazole; and
1-[4-(2-furyl)-2-hydroxy-n-butyl]imidazole.

PREPARATION 2

A solution of p-methoxybenzylmagnesium chloride is prepared from 97.2 g of magnesium turnings and p-methoxybenzyl chloride (32.78 g) in 440 ml ether according to the procedure described in The Journal of the American Chemical Society, 76, 1886 (1954), except that no iodine is used to initiate the reaction. The above solution is decanted under nitrogen into a pressure-equilibrated addition funnel above a flask containing epichlorohydrin (30.5 g) in ether (150 ml), the excess magnesium being washed with ether to ensure complete transfer of the Grignard reagent. The solution of p-methoxybenzylmagnesium chloride is then added dropwise with stirring under gentle reflux to the epichlorohydrin over about 40 minutes and stirring and reflux maintained for a further hour. The mixture is allowed to stand overnight. A saturated solution of ammonium chloride is added with stirring until no solid remains, whereupon the ether layer is separated and the aqueous phase re-extracted with ether. The combined extracts are washed with water, dried over MgSO$_4$, evaporated and the residue distilled in vacuo collecting the fraction of bp 140°–141° (0.3 mm Hg) to give 27.5 g of 1-chloro-4-(4-methoxyphenyl)-2-butanol as a colorless oil.

Similarly, proceeding as above, substituting the appropriately substituted benzyl chloride for p-methoxybenzyl chloride, there are prepared, for example, the following compounds:

1-chloro-4-(4-chlorophenyl)-2-butanol;
1-chloro-4-(4-fluorophenyl)-2-butanol;
1-chloro-4-(4-methylphenyl)-2-butanol;
1-chloro-4-(4-tert-butylphenyl)-2-butanol;
1-chloro-4-(4-ethoxyphenyl)-2-butanol;
1-chloro-4-(4-tert-butoxyphenyl)-2-butanol; and
1-chloro-4-(2,4-dichlorophenyl)-2-butanol.

PREPARATION 3

A solution of sodium imidazole is prepared by the portionwise addition of sodium hydride (6.77 g of 50% dispersion in mineral oil) to imidazole (10.8 g) in dry dimethylformamide (80 ml). The resulting mixture is treated dropwise with stirring at 50° with 1-chloro-4-(4-methoxyphenyl)-2-butanol (27.5 g) and the mixture stirred overnight at 50° and for six hours at 90°. The mixture is diluted with water (with stirring) to about 250 ml, hexane (50 ml) added whereupon the product started to precipitate. After the addition of water until no further turbidity results, the product is filtered off, washed well with cold water and hexane and dried in air. Recrystallization from ethyl acetate/hexane gives 1-[2-hydroxy-4-(4-methoxyphenyl)n-butyl]imidazole (21.2 g) as snow-white granules, mp 103°–105°.

Similarly, proceeding as above, substituting the appropriate chlorohydrin for 1-chloro-4-(4-methoxyphenyl)-2-butanol, there are prepared, for example, the following compounds:

1-[2-hydroxy-4-(4-chlorophenyl)-n-butyl]imidazole;
1-[2-hydroxy-4-(4-fluorophenyl)-n-butyl]imidazole;
1-[2-hydroxy-4-(4-methylphenyl)-n-butyl]imidazole;
1-[2-hydroxy-4-(4-tert-butylphenyl)-n-butyl]imidazole;
1-[2-hydroxy-4-(4-ethoxyphenyl)-n-butyl]imidazole;
1-[2-hydroxy-4-(4-tert-butoxyphenyl)-n-butyl]imidazole;
1-[2-hydroxy-4-(2,4-dichlorophenyl)-n-butyl]imidazole; and
1-[2-hydroxy-4-(4-trifluoromethylphenyl)-n-butyl]imidazole.

PREPARATION 4

1-[2-Hydroxy-4-(4-methoxyphenyl)-n-butyl]imidazole (2.0 g) is treated with thionyl chloride (10 ml) and the solution stirred for one hour at 60°. The solvent is evaporated under reduced pressure and the residue crystallized from ethyl acetate/ether, filtered, washed with ethyl acetate and dried in air to give 1-[2-chloro-4-(4-methoxyphenyl)-n-butyl]imidazole hydrochloride.

Similarly, proceeding as above, substituting the appropriate alcohol of formula (II) for 1-[2-hydroxy-4-(4-methoxyphenyl)-n-butyl]imidazole, there are prepared, for example, the hydrochloride salts of the following compounds:

1-[2-chloro-4-(4-chlorophenyl)-n-butyl]imidazole;
1-[2-chloro-4-(4-fluorophenyl)-n-butyl]imidazole;
1-[2-chloro-4-(4-methylphenyl)-n-butyl]imidazole;
1-[2-chloro-4-(4-tert-butylphenyl)-n-butyl]imidazole;
1-[2-chloro-4-(4-ethoxyphenyl)-n-butyl]imidazole;
1-[2-chloro-4-(4-tert-butoxyphenyl)-n-butyl]imidazole;
1-[2-chloro-4-(2,4-dichlorophenyl)-n-butyl]imidazole;
1-[2-chloro-4-(4-trifluoromethyphenyl)-n-butyl]imidazole;
1-[2-chloro-4-(2-thienyl)-n-butyl]imidazole;
1-[2-chloro-4-(3-thienyl)-n-butyl]imidazole;
1-[2-chloro-4-(5-methyl-2-thienyl)-n-butyl]imidazole;
1-[2-chloro-4-(4-methyl-2-furyl)-n-butyl]imidazole; and
1-[2-chloro-4-(5-chloro-2-thienyl)-n-butyl]imidazole.

PREPARATION 5

1-[2-Hydroxy-4-(4-chlorophenyl)-n-butyl]imidazole (2.0 g) in thionyl chloride (10 ml) is warmed for one hour at 65°. The excess thionyl chloride is removed in vacuo, the residue dissolved in dichloromethane (75 ml) and shaken with excess aqueous potassium carbonate. The organic layer is washed with water, dried over MgSO$_4$, evaporated and the residue evacuated to remove all traces of dichloromethane, affording 1-[2-chloro-4-(4-chlorophenyl)-n-butyl]imidazole.

Similarly, proceeding as above, substituting the appropriate alcohol of formula (II) for 1-[2-hydroxy-4-(4-chlorophenyl)-n-butyl]imidazole, there are prepared, for example, the following compounds:

1-[2-chloro-4-(4-methoxyphenyl)-n-butyl]imidazole;
1-[2-chloro-4-(4-fluorophenyl)-n-butyl]imidazole;

1-[2-chloro-4-(4-methylphenyl)-n-butyl]imidazole;
1-[2-chloro-4-(4-tert-butylphenyl)-n-butyl]imidazole;
1-[2-chloro-4-(4-ethoxyphenyl)-n-butyl]imidazole;
1-[2-chloro-4-(4-tert-butoxyphenyl)-n-butyl]imidazole;
1-[2-chloro-4-(2,4-dichlorophenyl)-n-butyl]imidazole;
1-[2-chloro-4-(2-thienyl)-n-butyl]imidazole;
1-[2-chloro-4-(3-thienyl)-n-butyl]imidazole;
1-[2-chloro-4-(5-methyl-2-thienyl)-n-butyl]imidazole;
1-[2-chloro-4-(5-methyl-2-furyl)-n-butyl]imidazole; and
1-[2-chloro-4-(5-chloro-2-thienyl(-n-butyl]imidazole.

EXAMPLE 1

A mixture of 1.25 g of 1-[2-hydroxy-4-(4-chlorophenyl)butyl]imidazole and 0.26 g of sodium hydride (50% dispersion in mineral oil) in 10 ml of dry hexamethylphosphoramide is stirred under nitrogen at room temperature for one hour and at 45° for one hour. After the evolution of hydrogen ceases, the solution is cooled in an ice bath and a solution of 1.00 g of 5-chloro-2-chloromethylthiophene in 2 ml hexamethylphosphoramide is added dropwise keeping the temperature below 10°. The solution is stirred for one hour at room temperature, 2 hours at 45° and allowed to stand overnight. The resulting mixture is then poured into water, extracted with ether, the ether extracts washed with water, dried and evaporated. The oily product, 1-[2-(5-chloro-2-thienylmethoxy)-4-(4-chlorophenyl)butyl]imidazole, is converted to its nitrate salt by treatment of an ethereal solution with concentrated nitric acid until precipitation is complete. The precipitate is collected and recrystallized from acetone as colorless crystals mp 121.5°124°.

In a similar manner are prepared the following compounds:

1-[4-(5-chloro-2-thienyl)-2-(4-chlorobenzyloxy)-n-butyl]imidazole;
1-[4-(5-chloro-2-thienyl)-2-(4-methoxybenzyloxy)-n-butyl]imidazole;
1-[4-(5-chloro-2-thienyl)-2-(4-methylbenzyloxy)-n-butyl]imidazole;
1-[4-(5-chloro-2-thienyl)-2-(2,4-dichlorobenzyloxy)-n-butyl]imidazole; and
1-[4-(5-chloro-2-thienyl)-2-(4-fluorobenzyloxy)-n-butyl]imidazole;
1-[4-(4-chlorophenyl)-2-(2-thienylmethoxy)-n-butyl]imidazole;
1-[4-(4-chlorophenyl)-2-(3-thienylmethoxy)-n-butyl]imidazole;
1-[4-(4-chlorophenyl)-2-(2-chloro-3-thienylmethoxy)-n-butyl]imidazole;
1-[4-(4-chlorophenyl)-2-(2,5-dichloro-3-thienylmethoxy)-n-butyl]imidazole;
1-[4-(4-chlorophenyl)-2-(5-methyl-2-thienylmethoxy)-n-butyl]imidazole;
1-[4-(4-chlorophenyl)-2-(2-furylmethoxy)-n-butyl]imidazole;
1-[4-(4-methylphenyl)-2-(5-chloro-2-thienylmethoxy)-n-butyl]imidazole;
1-[4-(2-thienyl)-2-(2,4-dichlorobenzyloxy)-n-butyl]imidazole;
1-[4-(5-methyl-2-thienyl)-2-(4-chlorobenzyloxy)-n-butyl]imadazole; and
1-[4-(4-methoxyphenyl)-2-(5-chloro-2-thienylmethoxy)-n-butyl]imidazole.

EXAMPLE 2

A mixture of 7.5 ml 1.6 M n-butyl lithium in hexane and 10 ml dry tetrahydrofuran under nitrogen at −78° is treated with 1.42 g of 2-chlorothiophene in 10 ml tetrahydrofuran (THF). The resulting light green solution is further treated with 0.32 g of sulfur and allowed to warm up to 0°. A solution of 1.35 g of 1-[4-(4-chlorophenyl)-2-chloro-n-butyl]imidazole in 10 ml dry THF is then added dropwise and the mixture stirred overnight at room temperature and at 60° for 4 hours. After removal of the solvent, water is added, the product extracted with ether and the extract washed, dried over MgSO$_4$ and evaporated. The resulting oil is chromatographed on silica gel, eluting with 6% methanol in dichloromethane and the product, 1-[4-(4-chlorophenyl)-2-(5-chloro-2-thienylthio)-n-butyl]imidazole is converted to the nitrate salt. Recrystallization from ethyl acetate affords the pure product, mp 83.5°–84.5°.

In a similar manner substituting furan for the 2-chlorothiophene in the above example there may be obtained 1-[4-(4-chlorophenyl)-2-(2-furylthio)-n-butyl]imidazole, nitrate salt mp 92.5°–94.5°.

Similarly prepared are the following:

1-[4-(4-chlorophenyl)-2-(2-thienylthio)-n-butyl]imidazole;
1-[4-(4-methylphenyl)-2-(5-chloro-2-thienylthio)-n-butyl]imidazole;
1-[4-(4-fluorophenyl)-2-(5-chloro-2-thienylthio)-n-butyl]imidazole;
1-[4-(4-methoxyphenyl)-2-(5-chloro-2-thienylthio)-n-butyl]imidazole;
1-[4-(4-chlorophenyl)-2-(5-methyl-2-furylthio)-n-butyl]imidazole;
1-[4-(4-chlorophenyl)-2-(3-chloro-2-thienylthio)-n-butyl]imidazole;
1-[4-(4-chlorophenyl)-2-(3-bromo-2-thienylthio)-n-butyl]imidazole;
1-[4-(4-trifluoromethylphenyl)-2-(5-chloro-2-thienylthio)-n-butyl]imidazole; and
1-[4-(4-chlorophenyl)-2-(3-methoxy-2-thienylthio)-n-butyl]imidazole.

EXAMPLE 3

Solid N-(2,6-dichlorophenylthio)succinimide (0.81 g) is added portionwise over one minute to a stirred mixture of 0.59 g of tri-n-butylphosphine and 0.50 g of 1-[4-(5-chloro-2-thienyl)-2-hydroxy-n-butyl]imidazole in 20 ml tetrahydrofuran. The mixture is stirred overnight under nitrogen at room temperature, the solvent removed, 200 ml ether added and the solution filtered. Dropwise addition of concentrated nitric acid (d=1.4) to the clear filtrate causes precipitation of 1-[4-(5-chloro-2-thienyl)-2-(2,6-dichlorophenylthio)-n-butyl]imidazole nitrate, recrystallized from ethanol with mp 147°–148.5° (dec).

Similarly prepared, substituting the appropriate succinimide for N-(2,6-dichlorophenylthio)succinimide are the following:

1-[4-(5-chloro-2-thienyl)-2-(2-chlorophenylthio)-n-butyl]imidazole;
1-[4-(5-chloro-2-thienyl)-2-(2,3-dichlorophenylthio)-n-butyl]imidazole;
1-[4-(5-chloro-2-thienyl)-2-(2,4-dichlorophenylthio)-n-butyl]imidazole;

1-[4-(5-chloro-2-thienyl)-2-(2,5-dichlorophenylthio)-n-butyl]imidazole;
1-[4-(5-chloro-2-thienyl)-2-(2,4,6-trichlorophenylthio)-n-butyl]imidazole; and
1-[4-(5-chloro-2-thienyl)-2-(2,4,5-trichlorophenylthio)-n-butyl]imidazole.

EXAMPLE 4

A mixture of 850 mg of 1-[4-(5-chloro-2-thienyl)-2-chloro-n-butyl]imidazole, 670 mg of 2-chlorothiophenol and 500 mg of potassium carbonate in 40 ml of acetone is stirred and refluxed for 4 hours. The solvent is evaporated under vacuum and 50 ml of water is added. The resulting mixture is extracted with ether and the ether extract is washed with water, dried and evaporated to afford 1-[2-(2-chlorophenylthio)-4-(5-chloro-2-thienyl)-n-butyl]imidazole as an oil. This material is converted to the nitrate salt by treatment with nitric acid, which salt is recrystallized from acetone/ethyl acetate as colorless flakes, mp 121°–122°.

In a similar manner are prepared the following compounds:

1-[4-(5-chloro-2-thienyl)-2-(2-methylphenylthio)-n-butyl]imidazole;
1-[4-(5-chloro-2-thienyl)-2-(2,4-dimethylphenylthio)-n-butyl]imidazole;
1-[4-(5-chloro-2-thienyl)-2-(2,5-dimethylphenylthio)-n-butyl]imidazole;
1-[4-(5-chloro-2-thienyl)-2-(2,6-dimethylphenylthio)-n-butyl]imidazole;
1-[4-(5-chloro-2-thienyl)-2-(2,4,6-trimethylphenylthio)-n-butyl]imidazole;
1-[4-(5-chloro-2-thienyl)-2-(2-ethylphenylthio)-n-butyl]imidazole;
1-[4-(5-chloro-2-thienyl)-2-(2-i-propylphenylthio)-n-butyl]imidazole;
1-[4-(5-chloro-2-thienyl)-2-(2-methoxyphenylthio)-n-butyl]imidazole;
1-[4-(5-chloro-2-thienyl)-2-(2,4-dimethoxyphenylthio)-n-butyl]imidazole;
1-[4-(5-chloro-2-thienyl)-2-(2-methyl-5-chlorophenylthio)-n-butyl]imidazole;
1-[4-(5-methyl-2-thienyl)-2-(2,6-dichlorophenylthio)-n-butyl]imidazole;
1-[4-(2-thienyl)-2-(2,6-dichlorophenylthio)-n-butyl]imidazole;
1-[4-(3-thienyl)-2-(2,6-dichlorophenylthio)-n-butyl]imidazole;
1-[4-(2-furyl)-2-(2,6-dichlorophenylthio)-n-butyl]imidazole;
1-[4-(5-methyl-2-furyl)-2-(2,6-dichlorophenylthio)-n-butyl]imidazole;
1-[4-(5-chloro-2-thienyl)-2-(2-methoxy-5-chlorophenylthio)-n-butyl]imidazole;
1-[4-(5-chloro-2-thienyl)-2-(2-chloro-5-methoxyphenylthio)-n-butyl]imidazole;
1-[4-(5-chloro-2-thienyl)-2-(2-chloro-4,5-dimethylphenylthio)-n-butyl]imidazole;
1-[4-(5-chloro-2-thienyl)-2-(2-chloro-6-methylphenylthio)-n-butyl]imidazole; and
1-[4-(4-chlorophenyl)-2-(3-thienylthio)-n-butyl]imidazole.

EXAMPLE 5

A solution of 1.35 g of 1-[2-chloro-4-(4-chlorophenyl)-n-butyl]imidazole in 10 ml tetrahydrofuran is added to a fully reacted mixture of 1.14 g of furfuryl mercaptan and 380 mg of 50% sodium hydride dispersion in mineral oil in 30 ml of tetrahydrofuran. After stirring under reflux for 12 hours the solvent is evaporated under vacuum and 150 ml of ether is added. The resulting mixture is washed twice with water and the ethereal solution dried and evaporated to afford crude 1-[2-(2-furylmethylthio)-4-(4-chlorophenyl)-n-butyl]imidazole as an oil. Chromatography on silica gel eluting with 30% acetone/CHCl$_2$ affords pure product, converted to the nitrate salt by dropwise treatment of an ethereal solution with concentrated nitric acid (d=1.4) until precipitation is complete. The collected precipitate is recrystallized from acetone/hexane to yield the nitrate salt, mp 97°–98°.

In a similar manner are prepared the following compounds:

1-[4-(5-chloro-2-thienyl)-2-(4-chlorobenzylthio)-n-butyl]imidazole;
1-[4-(5-chloro-2-thienyl)-2-(4-methylbenzylthio)-n-butyl]imidazole;
1-[4-(5-chloro-2-thienyl)-2-(4-methoxybenzylthio)-n-butyl]imidazole; and
1-[4-(5-chloro-2-thienyl)-2-(2,4-dichlorobenzylthio)-n-butyl]imidazole.

By substituting 1-[4-(5-methyl-2-thienyl)-2-hydroxy-n-butyl]imidazole, 1-[4-(2-thienyl)-2-hydroxy-n-butyl]imidazole or 1-[4-(3-thienyl)-2-hydroxy-n-butyl]imidazole for 1-[4-(5-chloro-2-thienyl)-2-hydroxy-n-butyl]imidazole in the above Example the compounds of formula (I) illustrated above can be prepared where $R^1$ is the 5-methyl-2-thienyl, 2-thienyl or 3-thienyl group.

EXAMPLE 6

A stirred room temperature solution of 1-[2-hydroxy-4-(5-chloro-2-thienyl)-n-butyl]imidazole (2.00 g) in dry tetrahydrofuran (30 ml) is treated successively with 2-chlorophenol (1.56 g), diethyl azodicarboxylate (2.10 g) and triphenylphosphine (3.15 g). After stirring overnight, the solution is evaporated to dryness, the residue dissolved in ether (125 ml) and the ethereal solution treated dropwise with 70% nitric acid (d=1.42) until precipitation is complete. The precipitate is collected and neutralized by stirring in 100 ml of ether with excess aqueous potassium carbonate until no solid remains. The ethereal layer is separated, dried over MgSO$_4$, evaporated and the residue chromatographed on silica gel eluting with acetone (2% to 30%) in dichloromethane. The pure product is again converted to the nitrate salt and the resulting precipitate of 1-[2-(2-chlorophenoxy)-4-(5-chloro-2-thienyl)-n-butyl]imidazole nitrate is filtered off and recrystallized from ethyl acetate.

In a similar manner are prepared the following compounds:

1-[4-(5-chloro-2-thienyl)-2-(2,4-dichlorophenoxy)-n-butyl]imidazole;
1-[4-(5-chloro-2-thienyl)-2-(2,5-dichlorophenoxy)-n-butyl]imidazole;
1-[4-(5-chloro-2-thienyl)-2-(2,6-dichlorophenoxy)-n-butyl]imidazole;
1-[4-(5-chloro-2-thienyl)-2-(2,4,6-trichlorophenoxy)-n-butyl]imidazole;
1-[4-(5-chloro-2-thienyl)-2-(2-methylphenoxy)-n-butyl]imidazole;
1-[4-(5-chloro-2-thienyl)-2-(2,5-dimethylphenoxy)-n-butyl]imidazole;

1-[4-(5-chloro-2-thienyl)-2-(2,6-dimethylphenoxy)-n-butyl]imidazole;
1-[4-(5-chloro-2-thienyl)-2-(2,4,6-trimethylphenoxy)-n-butyl]imidazole;
1-[4-(5-chloro-2-thienyl)-2-(2-i-propylphenoxy)-n-butyl]imidazole;
1-[4-(5-chloro-2-thienyl)-2-(2-methoxyphenoxy)-n-butyl]imidazole; and
1-[4-(5-chloro-2-thienyl)-2-(2-methyl-5-chlorophenoxy)-n-butyl]imidazole.

EXAMPLE 7

1,2-Epoxy-4-(4-chlorophenyl)butane (1.82 g) in dry tetrahydrofuran (10 ml) is added to the clear solution obtained from the reaction of 50 mg of 56% sodium hydride dispersion in mineral oil with 1.90 g of 5-chloro-2-thienylmethylmercaptan in 50 ml of dry tetrahydrofuran.

After stirring for four hours at 60° the solvent is removed, the residue treated with water and extracted with ether. The ether extract is dried and evaporated to afford a colorless oil.

The above oil in 30 ml dichloromethane is treated with 2 ml of thionyl chloride at room temperature for 30 minutes and the solution evaporated to dryness. The residue is treated with 4 g of imidazole and 15 ml of acetonitrile and stirred overnight at room temperature, then for one day at 50°. The solvent is evaporated and after the addition of 50 ml water the residue is extracted with ether. The ether extract is washed with water, dried and evaporated to afford crude 1-[2-(5-chloro-2-thienylmethylthio)-4-(4-chlorophenyl)-n-butyl-]imidazole which is converted to its nitrate salt and recrystallized from ethyl acetate.

EXAMPLE 8

Nitric acid (70%; d=1.42) is added dropwise to a stirred solution of 2.0 g of 1-[2-(2,6-dichlorophenylthio)-4-(5-chloro-2-thienyl)-n-butyl]imidazole in 30 ml of anhydrous ether until precipitation is complete. The product is filtered off, washed with ether, air dried and recrystallized from ethanol to yield 1-[2-(2,6-dichlorophenylthio)-4-(5-chloro-2-thienyl)-n-butyl]imidazole nitrate mp 147°–148.5° (dec.)

In a similar manner, all compounds of formula (I) in base form can be converted to their antimicrobial acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid or p-toluenesulfonic acid.

EXAMPLE 9

1-[2-(2,6-Dichlorophenylthio)-4-(5-chloro-2-thienyl)-n-butyl]imidazole nitrate (2.0 g) in 100 ml of dichloromethane is shaken with excess dilute potassium carbonate solution until the salt is completely dissolved. the organic layer is then separated, washed twice with water, dried over magnesium sulfate and evaporated to yield 2-[2-(2,6-dichlorophenylthio)-4-(5-chloro-2-thienyl)-n-butyl]imidazole as an oil.

In similar manner, the antimicrobial acid addition salts of all compounds of formula (I) can be converted to the corresponding compounds in base form.

EXAMPLE 10

The following illustrates the preparation of representative pharmaceutical formulations which may be used for controlling fungi, bacteria and protozoa, utilizing an active compound of formula (I) such as a salt of 1-[2-(2,6-dichlorophenylthio)-4-(5-chloro-2-thienyl)-n-butyl]imidazole.

| A. Topical Formulation | |
|---|---|
| | grams |
| Active compound | 0.2–2 |
| Span 60 | 2 |
| Tween 60 | 2 |
| Mineral oil | 5 |
| Petrolatum | 10 |
| Methyl paraben | 0.15 |
| propyl paraben | 0.05 |
| BHA (butylated hydroxy anisole) | 0.01 |
| Water | qs 100 |

All of the above ingredients, except water, are combined and heated at 60° with stirring. A sufficient quantity of water at 60° is then added with vigorous stirring to provide 100 g of the cream formulation which is then cooled to room temperature.

| B. I.V. Formulation | |
|---|---|
| Active compound | 0.5 g |
| Propylene glycol | 20 g |
| Polyethylene glycol 400 | 20 g |
| Tween 80 | 1 g |
| 0.9 Saline solution qs | 100 ml |

The active compound is dissolved in propylene glycol, polyethylene glycol 400 and Tween 80. A sufficient quantity of 0.9% saline solution is then added with stirring to provide 100 ml of the I.V. solution which is filtered through a 0.2 micron membrane filter and packaged under sterile conditions.

| C. Oral Formulation | |
|---|---|
| | parts by weight |
| Active compound | 200 |
| Magnesium stearate | 3 |
| Starch | 30 |
| Lactose | 116 |
| Polyvinylpyrrolidone | 3 |

The above ingredients are combined and granulated using methanol as the solvent. The formulation is then dried and formed into tablets (containing 200 mg of active compound) with an appropriate tabletting machine.

What is claimed is:

1. The compound of the formula

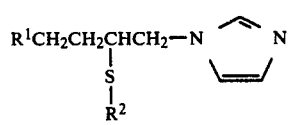

and the antimicrobial acid addition salts thereof wherein $R^1$ is optionally substituted furyl, the substituents independently selected from the group halo, $C_1$ to $C_6$ alkyl and $C_1$ to $C_6$ alkoxy; and $R^2$ is optionally substituted phenyl, the substituents independently selected from the group halo, $C_1$ to $C_4$ alkyl, $C_1$ to $C_4$ alkoxy and trifluoromethyl.

2. The compound of claim 1 wherein $R^1$ is 2-furyl or 5-methyl-2-furyl.

3. The compound of claim 2 that is 1-[4-(5-methyl-2-furyl)-2-(2,6-dichlorophenylthio)-n-butyl]imidazole and the antimicrobial acid addition salts thereof.

4. The compound of claim 2 that is 1-[4-(2-furyl)-2-(2,6-dichlorophenylthio)-n-butyl]imidazole and the antimicrobial acid addition salts thereof.

5. A composition useful for inhibiting the growth of fungi, bacteria or protozoa which comprises an antifungally, antibacterially or antiprotozoally effective amount of a compound of claim 1 in combination with a pharmaceutically acceptable diluent.

6. The composition of claim 5 for topical administration wherein the compound of formula (I) is present at between 0.1 and 10.0 weight percent of said composition.

7. A method for inhibiting the growth of fungi, bacteria or protozoa which comprises applying to a host containing or subject to attack by said fungi, bacteria or protozoa an antifungally, antibacterially or antiprotozoally effective amount of a compound of claim 1.

8. The method of claim 7 wherein the compound is administered topically.

9. The method of claim 7 wherein the compound is administered orally.

10. The method of claim 7 wherein the compound is administered parenterally.

* * * * *